United States Patent [19]
Hartmann

[11] Patent Number: 5,900,410
[45] Date of Patent: May 4, 1999

[54] MONOTHERAPY OF PEPTIC ULCERS AND GASTRITIS

[76] Inventor: John F. Hartmann, 1 Woodmeadow Ln., Princeton Junction, N.J. 08550-1323

[21] Appl. No.: 08/909,896

[22] Filed: Aug. 12, 1997

Related U.S. Application Data

[60] Provisional application No. 60/024,432, Aug. 27, 1996.
[51] Int. Cl.[6] ...................... A61K 31/675; C07F 9/6561; C07F 9/6558
[52] U.S. Cl. ............................... 514/81; 514/82; 544/337
[58] Field of Search ........................ 514/81, 82; 544/337

[56] References Cited

U.S. PATENT DOCUMENTS

| 5,409,903 | 4/1995 | Polak et al. | 514/23 |
| 5,476,669 | 12/1995 | Borody | 424/653 |
| 5,498,699 | 3/1996 | Djokic et al. | 534/15 |
| 5,674,858 | 10/1997 | McColm | 514/154 |

*Primary Examiner*—Michael G. Ambrose
*Attorney, Agent, or Firm*—D. J. Perrella

[57] ABSTRACT

The present invention is directed to compositions, methods and kits for treating areas of *H. pylori* infection in the GI tract. The active ingredient is an antibiotic-bisphosphonate adduct wherein the antibiotic is selected for its ability to eradicate *H. pylori*. Other components include a salt of a divalent cation that is insolubilized in vivo at alkaline pH, and optionally a substrate from which the enzyme urease liberates $NH_3$.

15 Claims, No Drawings

MONOTHERAPY OF PEPTIC ULCERS AND GASTRITIS

The present application claims priority from provisional application No. 60/024,432 filed Aug. 27, 1996.

The present invention relates to the treatment of ulcers in the upper gastrointestinal tract.

The treatment of ulcers in the upper gastro-intestinal (hereafter GI) tract has heretofore been carried out by the use of bland diets, alkaline agents and gastric acid suppressors. While these methods have some effectiveness in relieving the pain and discomfort associated with such ulcers, they have only treated the symptoms and have failed to address the underlying cause which has come to be recognized as infection with *Helicobacter pylori* (hereafter *H. pylori*). Antibiotic treatments intended to eliminate the *H. pylori* infection have depended upon systemic distribution of the antibiotic, that is to say, absorption from the intestine, distribution into the systemic circulation, delivery to the upper GI tract, and release into the lumen. This method involves the administration of high levels of the antibiotic and, in some cases the appearance of systemic side-effects, and/or the development of a drug-resistant strain of *H. pylori*.

It is, accordingly, an object of the present invention to provide a topical method for treating and ameliorating the infection that is responsible for gastritis and the formation of ulcers in the upper GI tract. Another object is to provide a method that does not require systemic administration of an antibiotic. A further object is to provide a kit containing the ingredients for carrying out the method of the present invention. Still another object is to provide compositions utilized in the method of the present invention. These and other objects of the present invention will be apparent from the following description.

The antibiotic-bisphosphonate adducts of the present invention can be prepared according to the methods disclosed in International Publications WO 96/09271 and WO 96/40190.

According to the present invention an ulcer patient is orally administered a mixture comprising (1) a solution of a divalent cation that is insoluble in vivo at alkaline pH, (2) an antibiotic-bisphosphonate adduct wherein the antibiotic is selected for its ability to eradicate *H. Pylori*, and (3) optionally a substrate from which the enzyme urease, located on the surface of the *H. pylori* bacterium, generates $NH_3$. The $NH_3$ creates, at sites of *H. pylori* infection, a localized environment that is sufficiently alkaline to precipitate the salt of the divalent cation directly onto the *H. pylori* bacterium. The bisphosphonate moiety of the antibiotic-bisphosphonate adduct is attracted to and concentrates on the surface of the various salt crystals, carrying with it the antibiotic group. Because the distribution of *H. pylori* in the gastric mucosa is "patchy", that is to say discontinuous, the distribution of pockets of alkaline pH and the crystals within them will be similar. As a consequence, the bacteria associated with the precipitated salts are exposed to an elevated level of the antibiotic-bisphosphonate adduct relative to its concentration in the surrounding milieu.

The ingredients of the mixture can be administered either sequentially or simultaneously as a composition that can be in any of several forms, for example as a liquid mixture or a gel. Examples of an antibiotic-bisphosphonate adduct wherein the antibiotic is selected for its ability to eradicate *H. Pylori* are 6-fluoro-1-ethyl-7-{4-[2,2-bis(diethoxyphosphono)-1-ethyl]-1-piperazyl}-4-oxo-1,4-dihydroquinoline-3-carboxylic acid, 1-cyclopropyl-7-{4-[3-hydroxy-3,3-bis(dimethoxy-phosphono)-1-propyl]-1-piperazyl}-4-oxo-1,4-dihydro-1,6-naphthyridine-3-carboxylic acid, 7-(4-methylpiperazino)-1-cyclopropyl-4-oxo-1,4-dihydro-1,6-naphthyridine-3-{N-[5-hydroxy-5,5-bis(dimethoxyphosphono)-pentyl]-carboxamide}], 1-cyclopropyl-6-fluoro-7-{4-[3-hydroxy-3,3-bis(dimethoxyphosphono)-1-propyl]-1-piperazyl}-1,4-dihydro-4-oxoquinoline-3-carboxylic acid, 1-cyclopropyl-6-fluoro-7-{4-[2,2-bis(diethoxy-phosphono)-1-ethyl]-1-piperazyl}-4-oxo-1,4-dihydroquinoline-3-carboxylic acid, or 1-cyclopropyl-6-fluoro-7-{4-[3,3-bis(diethoxyphosphono)-1-propyl]-1-piperazyl}-4-oxo-1,4-dihydroquinoline-3-carboxylic acid.

The antibiotic-bisphosphonate adduct is used at a dosage level that, is about the same as that at which the antibiotic component is used alone, although its optimal level may be greater or smaller.

The divalent cat ions can be, for example, Ba, Bi, Ca, Mg, and Sr. The anions associated with these cations to form the salt can be, for example, phosphate, carbonate, salicylate and citrate. Examples of some specific salts are $CaCO_3$, $CaHPO_4$, $Ca(OH)(PO_4)_3$, $Mg(OH)_2$, $MgNH_4PO_4 \cdot 6H_2O$ (struvite), $Ca_{10}[PO_4]_6CO_3$) (carbonate apatite), $BiHPO_4$, bismuth-subsalicylate, bismuth subcitrate and colloidal forms thereof, and tripotassium dicitrato bismuthate. Because these salts usually have low solubility in water, it is generally desirable to dissolve them in dilute acid solution. While the amount of the salt of the divalent cation is not critical, it is generally employed in an amount of from about 0.05 g to about 2.5 g.

The substrate is a compound from which urease liberates $NH_3$. A preferred substrate is urea. The amount of this substrate, when employed, may be from about 50 g to about 500 g. Other substrates can be employed in equivalent amounts. Where the amount of endogenous substrate (urea) naturally present in the upper GI tract is sufficient to liberate enough $NH_3$ to precipitate the salt of the divalent cation, it is possible that no substrate may have to be added. Preferably, however, some substrate will be added to insure that the amount of $NH_3$ liberated in vivo will be sufficient to precipitate the salt of the divalent cation. It is within the scope of the present invention to employ more than one substrate, or more than one salt, or more than one antibiotic-bisphosphonate adduct.

The method of the present invention is not only the first practical topical method to successfully treat *H. pylori* in the upper GI tract, but it also circumvents the shortcomings in all of the existing methods of treating *H. pylori* infection. The method of the present invention not only delivers via the highly desirable oral route high doses of antibiotic at the site of infection, thereby reducing the risk of development of resistance and increasing the effectiveness of the treatment, but also results in better patient compliance by simplifying the treatment regimen and reducing the time of treatment.

The following examples illustrate the present invention without, however, limiting the same thereto.

EXAMPLES 1–5

A series of *H. pylori* treatment kits are prepared containing the following unit dosage ingredients, or multiples thereof.

1. a) 6-fluoro-1-ethyl-7-{4-[2,2-bis(diethoxyphosphono)-1-ethyl]-1-piperazyl}-4-oxo-1,4-dihydroquinoline-3-carboxylic acid, 1 g, dissolved in 100 ml $H_2O$.
   b) $CaHPO_4$, 0.5 g, dissolved in 0.1 N HCl, 100 ml c) Urea, 250 g dissolved in 250 ml of 0.1 N citric acid.
2. a) 1-cyclopropyl-7-{4-[3-hydroxy-3,3-bis(dimethoxyphosphono)-1-propyl]-1-piperazyl}-4-oxo-1,4-dihydro-1,6-naphthyridine-3-carboxylic acid, 0.5 g
b) Ca(OH)(PO$_4$)$_3$, 2 g dissolved in 0.1 N HCl, 100 ml
c) Urea, 200 g dissolved in 200 ml of 0.05 N citric acid.
3. a) 7-(4-methylpiperazino)-1-cyclopropyl-4-oxo-1,4-dihydro-1,6-naphthyridine-3-{N-[5-hydroxy-5,5-bis(dimethoxyphosphono)pentyl]-carboxamide}], 0.1 g.
b) MgNH$_4$PO$_4$.6H$_2$O, 1.5 g dissolved in 0.1 N HCl, 100 ml
c) Urea, 100 g dissolved in 100 ml of 0.05 N citric acid.
4. a) 1-cyclopropyl-6-fluoro-7-{4-[3-hydroxy-3,3-bis(dimethoxyphosphono)-1-propyl]-1-piperazyl}-1,4-dihydro-4-oxo-quinoline-3-carboxylic acid, 0.75 g
b) Mg(OH)$_2$, 0.1 g
c) Urea, 50 g dissolved in 50 ml of 0.05 N citric acid.
5. a) 1-cyclopropyl-6-fluoro-7-{4-[2,2-bis(diethoxyphosphono)-1-ethyl]-1-piperazyl}-4-oxo-1,4-dihydroquinoline-3-carboxylic acid, 0.25 g
b) BiHPO$_4$, 1 g
c) Urea, 25 g dissolved in 50 ml of 0.05 N citric acid.
6. a) 1-cyclopropyl-6-fluoro-7-{4-[3,3-bis(diethoxyphosphono)-1-propyl]-1-piperazyl}-4-oxo-1,4-dihydroquinoline-3-carboxylic acid, 0.5 g
b) Ca$_{10}$[PO$_4$]$_6$CO$_3$, 0.25 g dissolved in 0.1 N HCl, 100 ml
c) Urea, 125 g dissolved in 100 ml of 0.05 N citric acid.

The foregoing formulations can be administered to ulcer patients either simultaneously or sequentially. In the latter case, the urea is usually administered first, followed within about 30 minutes, typically within from about 15 to about 30 minutes by the solution of the divalent cation, and then within about 30 minutes, typically within from about 15 to about 30 minutes by the antibiotic-bisphosphonate adduct.

What is claimed is:

1. A kit for treating areas of *H. Pylori* infection in the GI tract comprising unit dosage amounts of an antibiotic-bisphosphonate adduct wherein the antibiotic is selected for its ability to eradicate *H. Pylori*, a salt of a divalent cation that is insolubilized in vivo at alkaline pH, and optionally a substrate from which the enzyme urease liberates NH$_3$.

2. A kit according to claim 1 wherein the antibiotic-bisphosphonate adduct is 6-fluoro-1-ethyl-7-{4-[2,2-bis(diethoxyphosphono)-1-ethyl]-1-piperazyl}-4-oxo-1,4-dihydroquinoline-3-carboxylic acid, 1-cyclopropyl-7-{4-[3-hydroxy-3,3-bis(dimethoxy-phosphono)-1-propyl]-1-piperazyl}-4-oxo-1,4-dihydro-1,6-naphthyridine-3-carboxylic acid, 7-(4-methylpiperazino)-1-cyclopropyl-4-oxo-1,4-dihydro-1,6-naphthyridine-3-{N-[5-hydroxy-5,5-bis(dimethoxyphosphono)pentyl]-carboxamide}], 1-cyclopropyl-6-fluoro-7-{4-[3-hydroxy-3,3-bis(dimethoxyphosphono)-1-propyl]-1-piperazyl}-1,4-dihydro-4-oxo-quinoline-3-carboxylic acid, 1-cyclopropyl-6-fluoro-7-{4-[2,2-bis(diethoxy-phosphono)-1-ethyl]-1-piperazyl}-4-oxo-1,4-dihydroquinoline-3-carboxylic acid, or 1-cyclopropyl-6-fluoro-7-{4-[3,3-bis(diethoxyphosphono)-1-propyl]-1-piperazyl}-4-oxo-1,4-dihydroquinoline-3-carboxylic acid.

3. A kit according to claim 1 wherein the divalent cations are Ba, Bi, Ca, Mg, and Sr and the anions associated therewith are phosphate, carbonate, salicylate and citrate.

4. A kit according to claim 1 wherein the substrate is present.

5. A kit according to claim 4 wherein the substrate is urea.

6. A composition for treating areas of *H. Pylori* infection in the GI tract comprising an antibiotic-bisphosphonate adduct wherein the antibiotic is selected for its ability to eradicate *H. Pylori*, a salt of a divalent cation that is insolubilized in vivo at alkaline pH, and optionally a substrate from which the enzyme urease liberates NH$_3$.

7. A composition according to claim 6 wherein the antibiotic-bisphosphonate adduct is 6-fluoro-1-ethyl-7-{4-[2,2-bis(diethoxyphosphono)-1-ethyl]-1-piperazyl}-4-oxo-1,4-dihydroquinoline-3-carboxylic acid, 1-cyclopropyl-7-{4-[3-hydroxy-3,3-bis(dimethoxy-phosphono)-1-propyl]-1-piperazyl}-4-oxo-1,4-dihydro-1,6-naphthyridine-3-carboxylic acid, 7-(4-methylpiperazino)-1-cyclopropyl-4-oxo-1,4-dihydro-1,6-naphthyridine-3-{N-[5-hydroxy-5,5-bis(dimethoxyphosphono)pentyl]-carboxamide}], 1-cyclopropyl-6-fluoro-7-{4-[3-hydroxy-3,3-bis(dimethoxyphosphono)-1-propyl]-1-piperazyl}-1,4-dihydro-4-oxo-quinoline-3-carboxylic acid, 1-cyclopropyl-6-fluoro-7-{4-[2,2-bis(diethoxy-phosphono)-1-ethyl]-1-piperazyl}-4-oxo-1,4-dihydroquinoline-3-carboxylic acid, or 1-cyclopropyl-6-fluoro-7-{4-[3,3-bis(diethoxyphosphono)-1-propyl]-1-piperazyl}-4-oxo-1,4-dihydroquinoline-3-carboxylic acid.

8. A composition according to claim 6 wherein the divalent cations are Ba, Bi, Ca, Mg, and Sr and the anions associated therewith are phosphate, carbonate, salicylate and citrate.

9. A composition according to claim 6 wherein the substrate is present.

10. A composition according to claim 9 wherein the substrate is urea.

11. A method for treating localized areas of *H. Pylori* infection in the GI tract comprising introducing into the GI tract an antibiotic-bisphosphonate adduct wherein the antibiotic is selected for its ability to eradicate *H. Pylori*, a salt of a divalent cation that is insolubilized in vivo at alkaline pH, and optionally a substrate from which the enzyme urease liberates NH$_3$.

12. A method according to claim 11 wherein the antibiotic introduced into the GI tract is 6-fluoro-1-ethyl-7-{4-[2,2-bis(diethoxyphosphono)-1-ethyl]-1-piperazyl}-4-oxo-1,4-dihydroquinoline-3-carboxylic acid, 1-cyclopropyl-7-{4-[3-hydroxy-3,3-bis(dimethoxy-phosphono)-1-propyl]-1-piperazyl}-4-oxo-1,4-dihydro-1,6-naphthyridine-3-carboxylic acid, 7-(4-methylpiperazino)-1-cyclopropyl-4-oxo-1,4-dihydro-1,6-naphthyridine-3-{N-[5-hydroxy-5,5-bis(dimethoxyphosphono)pentyl]-carboxamide}], 1-cyclopropyl-6-fluoro-7-{4-[3-hydroxy-3,3-bis(dimethoxyphosphono)-1-propyl]-1-piperazyl}-1,4-dihydro-4-oxo-quinoline-3-carboxylic acid, 1-cyclopropyl-6-fluoro-7-{4-[2,2-bis(diethoxy-phosphono)-1-ethyl]-1-piperazyl}-4-oxo-1,4-dihydroquinoline-3-carboxylic acid, or 1-cyclopropyl-6-fluoro-7-{4-[3,3-bis(diethoxyphosphono)-1-propyl]-1-piperazyl}-4-oxo-1,4-dihydro-quinoline-3-carboxylic acid.

13. A method according to claim 11 wherein the salt of a divalent cation that is insolubilized at alkaline pH after being introduced into the GI tract is a salt containing a Ba, Bi, Ca, Mg, or Sr cation and a phosphate, carbonate, salicylate or citrate anion.

14. A method according to claim 11 including the step of introducing a substrate into the GI tract.

15. A method according to claim 14 wherein the substrate is urea.

* * * * *